US012263282B2

(12) United States Patent
Ching et al.

(10) Patent No.: US 12,263,282 B2
(45) Date of Patent: Apr. 1, 2025

(54) WIRELESS DIFFUSER WITH ONE-TIME-USE CONTAINER (71) Applicant: Aroma360, LLC, Miami, FL (US)

(72) Inventors: Oliver Ching, Jupiter, FL (US); Benzion Aboud, Miami, FL (US)

(73) Assignee: AROMA360, LLC, Miami, FL (US)

( * ) Notice: Subject to any disclaimer, the term of this patent is extended or adjusted under 35 U.S.C. 154(b) by 0 days.

(21) Appl. No.: 18/602,747

(22) Filed: Mar. 12, 2024

(65) Prior Publication Data

US 2024/0415998 A1 Dec. 19, 2024

Related U.S. Application Data (63) Continuation of application No. 18/210,444, filed on Jun. 15, 2023.

(51) Int. Cl.
*A61L 9/12* (2006.01)
(52) U.S. Cl.
CPC ........... *A61L 9/12* (2013.01); *A61L 2209/133* (2013.01)
(58) Field of Classification Search
CPC ................ A61L 9/12; A61L 2209/133
See application file for complete search history.

(56) References Cited

U.S. PATENT DOCUMENTS

| | | | |
|---|---|---|---|
| 3,633,822 A | 1/1972 | Hruby, Jr. | |
| 5,016,781 A * | 5/1991 | Ten Wolde | B05B 11/1052 222/162 |
| 6,929,154 B2 * | 8/2005 | Grey | B65D 83/386 222/402.1 |
| 7,297,211 B2 | 11/2007 | Cooper et al. | |
| 7,854,393 B2 | 12/2010 | DiBello et al. | |
| 7,878,418 B2 | 2/2011 | Sevy | |
| 9,156,045 B1 | 10/2015 | Preston et al. | |
| 9,211,357 B1 | 12/2015 | Li | |
| 9,458,615 B2 | 10/2016 | Carpenter et al. | |
| 9,539,355 B2 | 1/2017 | Hsiao | |
| 9,914,145 B2 | 3/2018 | Osborn et al. | |
| 11,154,633 B2 | 10/2021 | Hsiao | |
| 11,197,941 B1 | 12/2021 | Gao | |
| 11,224,674 B2 | 1/2022 | Song | |
| 11,707,092 B2 | 7/2023 | Plattner et al. | |

(Continued)

FOREIGN PATENT DOCUMENTS

| | | | |
|---|---|---|---|
| AU | 2021252180 A1 | 11/2022 | |
| CN | 116713139 A | 9/2023 | |

(Continued)

*Primary Examiner* — Sean E Conley
*Assistant Examiner* — Brendan A Hensel
(74) *Attorney, Agent, or Firm* — POLSINELLI PC (57) ABSTRACT

Disclosed herein is an electronic diffuser system incorporating a diffuser body and a wireless charging base. The diffuser body has an upper portion coupled to a lower portion. The upper portion has an inner connector and an outer connector. The lower portion has an upper connector at a top end configured to connect to the outer connector of the upper portion and defining an inner cavity having an opening at the top end. The system includes a one-time-use fragrance container configured to attach to the inner connector of the upper portion and fit into the inner cavity of the lower portion. The one-time-use fragrance container having an atomizer that is irremovably disposed within the fragrance container.

18 Claims, 8 Drawing Sheets

(56) References Cited

U.S. PATENT DOCUMENTS

| | | |
|---|---|---|
| 11,730,846 B2 | 8/2023 | Connors et al. |
| 2004/0050948 A1 | 3/2004 | Bartels |
| 2005/0150971 A1 | 7/2005 | Zhou |
| 2005/0196345 A1 | 9/2005 | Diederichs et al. |
| 2007/0031343 A1 | 2/2007 | Bonfour et al. |
| 2007/0137561 A1 | 6/2007 | Osako et al. |
| 2008/0277501 A1* | 11/2008 | Everett .................. B65D 83/14 251/129.15 |
| 2009/0072783 A1* | 3/2009 | Gaspar .................. A01M 1/205 320/108 |
| 2012/0018530 A1 | 1/2012 | Blaylock et al. |
| 2016/0144064 A1 | 5/2016 | Santini et al. |
| 2017/0252523 A1 | 9/2017 | Blakey et al. |
| 2017/0319730 A1 | 11/2017 | Nwachukwu et al. |
| 2017/0333648 A1 | 11/2017 | Cashman et al. |
| 2019/0290797 A1 | 9/2019 | Sevy |
| 2021/0046256 A1 | 2/2021 | Hoffman et al. |
| 2021/0046497 A1 | 2/2021 | Hoffman et al. |
| 2021/0260233 A1 | 8/2021 | Häussermann et al. |
| 2022/0015357 A1 | 1/2022 | Semoff et al. |
| 2022/0072183 A1 | 3/2022 | Zou et al. |
| 2023/0118045 A1 | 4/2023 | Danek |
| 2023/0120891 A1 | 4/2023 | Oliver et al. |
| 2023/0277711 A1* | 9/2023 | Lekach .................. A61L 9/037 422/119 |
| 2023/0310682 A1 | 10/2023 | Häussermann et al. |
| 2023/0321306 A1 | 10/2023 | Gao |

FOREIGN PATENT DOCUMENTS

| | | |
|---|---|---|
| EP | 1382399 B2 | 9/2015 |
| EP | 2675489 B1 | 10/2017 |
| EP | 2409716 B1 | 3/2018 |
| FR | 2860721 A1 | 4/2005 |
| GB | 525736 A | 9/1940 |
| GB | 674406 A | 6/1952 |
| GB | 2608465 B | 8/2023 |
| KR | 200485094 Y1 | 11/2017 |
| WO | 2013128104 A1 | 9/2013 |
| WO | 2018185694 A1 | 10/2018 |
| WO | 2021245390 A1 | 12/2021 |
| WO | 2023056498 A1 | 4/2023 |
| WO | 2023062560 A1 | 4/2023 |
| WO | 2023233381 A1 | 12/2023 |

* cited by examiner

WIRELESS DIFFUSER WITH ONE-TIME-USE CONTAINER

CROSS REFERENCE TO RELATED APPLICATIONS

The present application is a continuation of U.S. patent application Ser. No. 18/210,444 filed Jun. 15, 2023, the disclosure of which is hereby incorporated by reference herein.

BACKGROUND OF THE INVENTION

Diffusers are common household products that users employ to disperse essential oils through clouds of vapor. While this can be done in a variety of ways, fluid atomizers are one common way of diffusing scented oils. A common arrangement for atomize diffusers is to have an oil reservoir with a means of transferring oil, e.g., small tube or pipette, from the oil reservoir to a diffusing mechanism, e.g., an atomizer, so it can be vaporized. When the oil reservoir is empty, the user commonly refills it. During this process, residual oil frequently drips from components that extend into the reservoir as diffuser components are separated, which can create a gummy mess over time. Therefore, there remains a need for a device that allows users to reload oil into a diffuser in a drip-free manner.

For those selling diffuser products, offering oil refills is a great way to encourage further business from customers and to ensure high quality oils are used. However, customers sometimes turn to third parties to purchase essential oils, even low-cost essential oils, to refill their diffusers. This potentially leads some customers to use low quality essential oils that may contain harmful chemicals and/or introduce liquids that could impair the function of their diffusers. Therefore, there is a need to ensure high quality replacement oil for diffusers and increase returning business.

BRIEF SUMMARY OF THE INVENTION

In accordance with an aspect, a diffuser may be configured with a one-time-use container disposed within a cavity of the diffuser. The one-time-use container is initially filled with oil, e.g., essential oil, and sealed with a cap that is irremovably attached, e.g., with a bonding agent and/or press fit, to the only opening of the container. Once the initial quantity of oil is vaporized, the cap prevents a user from refilling the container with replacement oil and requires the user to obtain a one-time-use replacement container to continue to use the diffuser. The cap may include a diffuser mechanism, e.g., an atomizer configured for cold-air diffusion, housed in an internal portion, a small tube extending therefrom, and an oil regulator attached to an end of the small tube. Once all the components of the cap are assembled and/or bonded together, the cap is irreversible installed in a hole of the container. Once the cap is installed, the container becomes a one-time-use container, which can then be attached, e.g., threadably engaged, with a portion of a diffuser specifically designed to receive such containers.

In another aspect, a diffuser apparatus may include an upper portion, a lower portion, and a one-time-use fragrance. The upper portion may include an inner connector and an outer connector. The lower portion may include an upper connector at a top end that may be configured to connect to the outer connector of the upper portion and may define an inner cavity having an opening at the top end. The one-time-use fragrance container may be configured to attach to the inner connector of the upper portion and may fit into the inner cavity of the lower portion such that the atomizer is irremovably disposed within the one-time-use fragrance container.

In some arrangements, the one-time-use fragrance container may include a plug that may be configured to house the atomizer and may prevent a user from refilling the one-time-use fragrance container. Additionally, the plug may be inseparable from the one-time-use container. In some such arrangements, a hollow cylinder open at both ends may extend from the atomizer such that the hollow cylinder extends towards a bottom of the one-time-use fragrance container. The hollow cylinder may define a top opening and a bottom opening. In such arrangements, a regulator may be disposed at the bottom opening of the hollow cylinder. In some such arrangements, the plug and the one-time-use fragrance container may be press-fit together such that a first portion and a second portion of the plug are inserted into an aperture of the one-time-use container. The first portion may define a larger diameter than the second portion. In some such arrangements, the larger diameter of the first portion may be at least 1 mm greater than a diameter defined by the second portion of the plug.

In some arrangements, the diffuser apparatus may further include a base portion connected to a bottom end of the lower portion such that a longitudinal axis of the base portion is perpendicular to a longitudinal axis of the lower portion. The base portion may enable the lower portion to stand on a surface such that the longitudinal axis of the lower portion is perpendicular to the surface while the longitudinal axis of the base portion lies parallel to the surface. In some such arrangements, the diffuser apparatus may further include a battery disposed within the lower portion such that the battery is configured to power the diffuser. In such arrangements, the battery may be a rechargeable battery. In such arrangements, the rechargeable battery may be configured to be recharged by an induction charger. In such arrangements, the induction charger may include a outer frame with a shallow basin configured to receive the base portion.

In some arrangements, the one-time-use fragrance container is a bottle with a volume of at least 60 mL. In some arrangements, the one-time-use fragrance container threadably attaches to the inner connector of the upper portion.

In some arrangements, the one-time-use fragrance container includes a plug that is press-fit into an aperture of the one-time-use fragrance container, the plug defining an outer portion and an inner portion such that the inner portion may house an atomizer having a hollow cylinder open at both ends extend therefrom. The hollow cylinder may have a regulator attached to a bottom opening of the hollow cylinder. The atomizer, hollow cylinder, and regulator may be in communication such that a liquid can enter the regulator and flow to the atomizer through the hollow cylinder.

In accordance with another aspect, a diffuser may be reloaded by a process. In the process, a lower portion of the diffuser may be detached from an upper portion. Next, the lower portion may be separated from the upper portion such that a first fragrance container attached to the upper portion is exposed, the first fragrance may be housing a first atomizer such that the first fragrance container and the first atomizer are inseparable. Then the first fragrance container may be detached from the upper portion. Subsequently, a second fragrance container housing a second atomizer may be attached to the upper portion, and then the lower portion may be reattached to the upper portion of the diffuser. The second fragrance atomizer may be inseparably connected to the second fragrance container. In some such arrangements, the process may further include the diffuser being placed on an induction charger configured to wirelessly recharge a battery housed in the diffuser.

In accordance with another aspect, a diffuser system may include a diffuser, a one-time-use fragrance container, and some quantity of scented liquid disposed in the one-time-use fragrance container. The diffuser may include an upper portion, a lower portion, and a battery. The upper portion may include an inner connector and an outer connector. The lower portion may include an upper connector at a top end configured to connect to the outer connector of the upper portion and may define an inner cavity having an opening at the top end of the lower portion. The battery may be housed within the lower portion. The one-time-use fragrance container may be configured to attach to the inner connector of the upper portion and may fit within the inner cavity of the lower portion. Additionally, the one-time-use fragrance container may house an atomizer that is inseparably connected to the one-time-use fragrance container. In some such arrangements, the diffuser system may include a one-time-use replacement container that may house a replacement atomizer. The one-time-use replacement container may be configured to attach to the inner connector of the upper portion after the one-time-use fragrance container is detached from the upper portion of the diffuser. In some such arrangements, the one-time-use fragrance container and the one-time-use replacement container contain different scented liquids. Additionally, the one-time-use fragrance container and the one-time-use replacement container may be configured such that an attempt to refill the one-time-use container by removing a plug containing the atomizer from the one-time-use fragrance container renders the one-time-use container inoperable with the diffuser system. In some such arrangements, the battery in the diffuser system may be a rechargeable battery. In some such arrangements, the diffuser system may include an induction charger configured to wirelessly charge the rechargeable battery.

BRIEF DESCRIPTION OF THE DRAWINGS

A more complete appreciation of the subject matter of the present disclosure and the various advantages thereof may be realized by reference to the following detailed description which refers to the accompanying drawings, in which.

DETAILED DESCRIPTION

This disclosure relates to a diffuser that is configured to use an oil container that cannot be refilled or reused, i.e., a one-time-use container. The various embodiments described herein refer to electronic diffusers powered by either a battery or a power outlet. Additionally, the method of diffusion may include, but is not limited to, ultrasonic or nebulizer (e.g., atomization).

Figure 1:
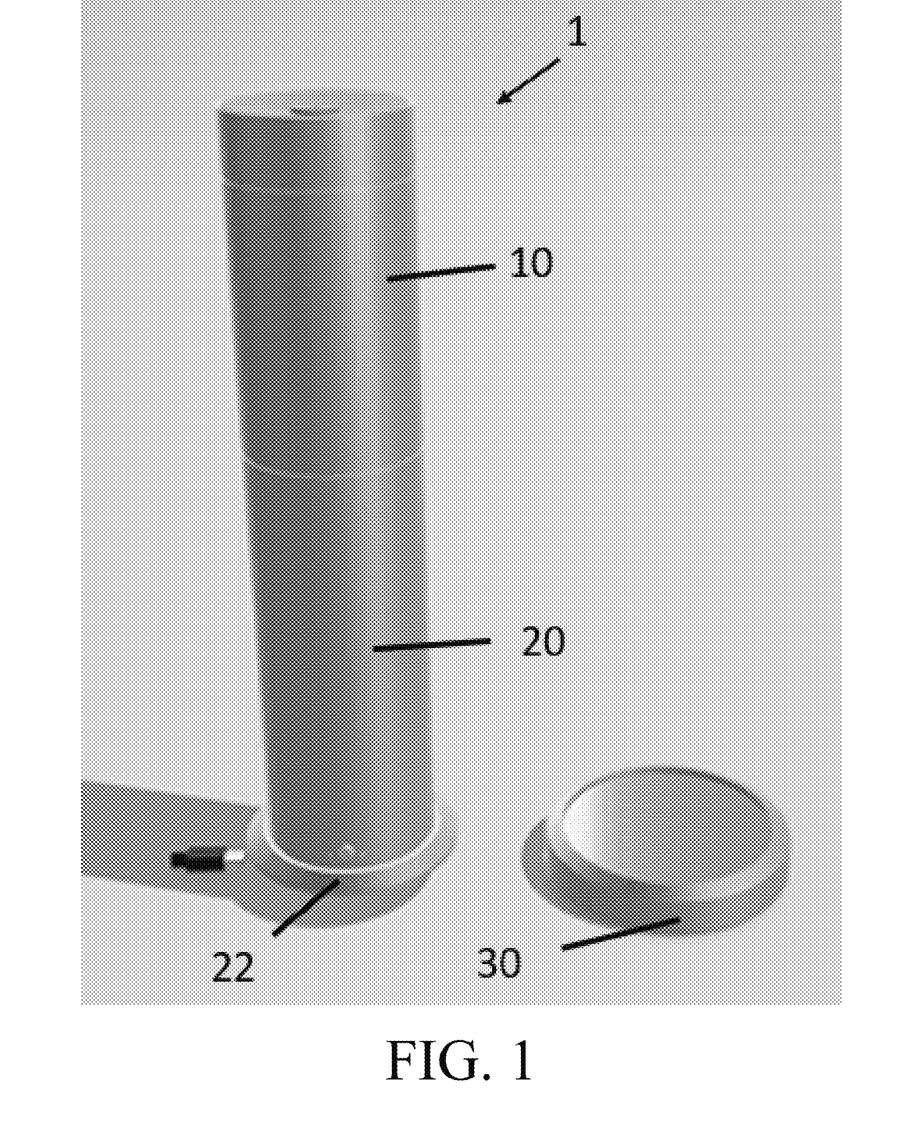
FIG. 1 is a perspective view of a diffuser, in accordance with an aspect.
Figure 2:
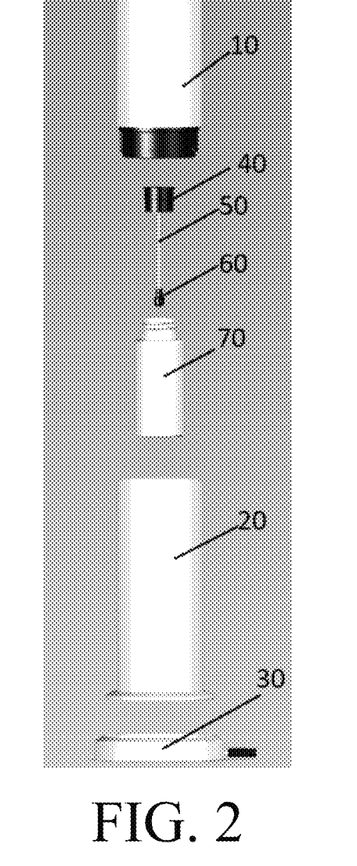
FIG. 2 is an exploded view of the diffuser of FIG. 1.
Figure 11:
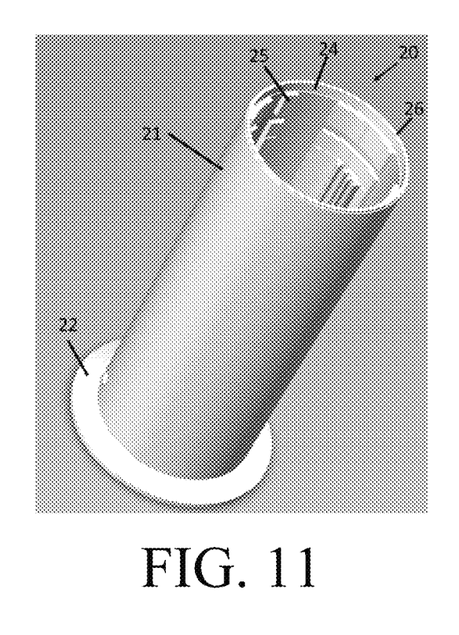
FIG. 11 is a perspective view of a lower portion of the diffuser of FIG. 1.

Referring now to the drawings, as shown in FIGS. 1-2, diffuser 1 may include upper portion 10, lower portion 20 that supports and connects to upper portion 10, and charger 30. Upper portion 10 and lower portion 20 may have the same outer diameter such that they may house various internal components of diffuser 1, for example, but not limited to, plug 40, pipette 50, regulator 60, and container 70. Pipette 50 may have two open ends and may be configured to extend from or attach to plug 40 at one end such that regulator 60 may be attached at the other end of pipette 50. Container 70 may be configured to receive regulator 60, pipette 50, and plug 40 all attached together. Plug 40 may be configured to attach to container 70 in an undetachable manner (disclosed in more detail below). Lower portion may be configured to receive and house container 70 in inner cavity 24 (as shown in FIG. 11) such that when diffuser 1 is assembled, the majority of container 70 is located within inner cavity 24 of lower portion 20, and upper portion 10 may be configured to engage and connect with a portion of container 70 such that the container may detachably attach to the upper portion.

Figure 3:
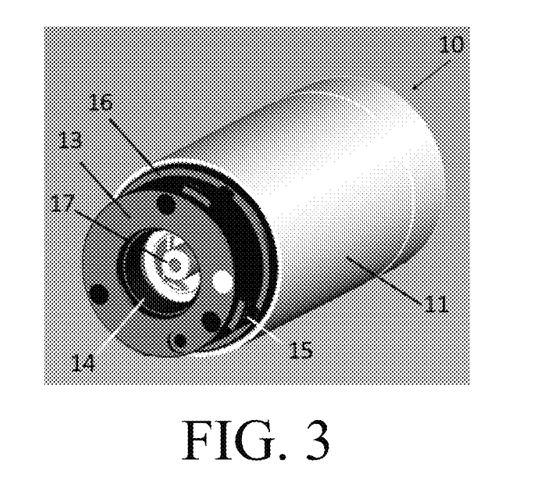
FIG. 3 is a perspective view of an upper portion of a diffuser, in accordance with an aspect.
Figure 4:
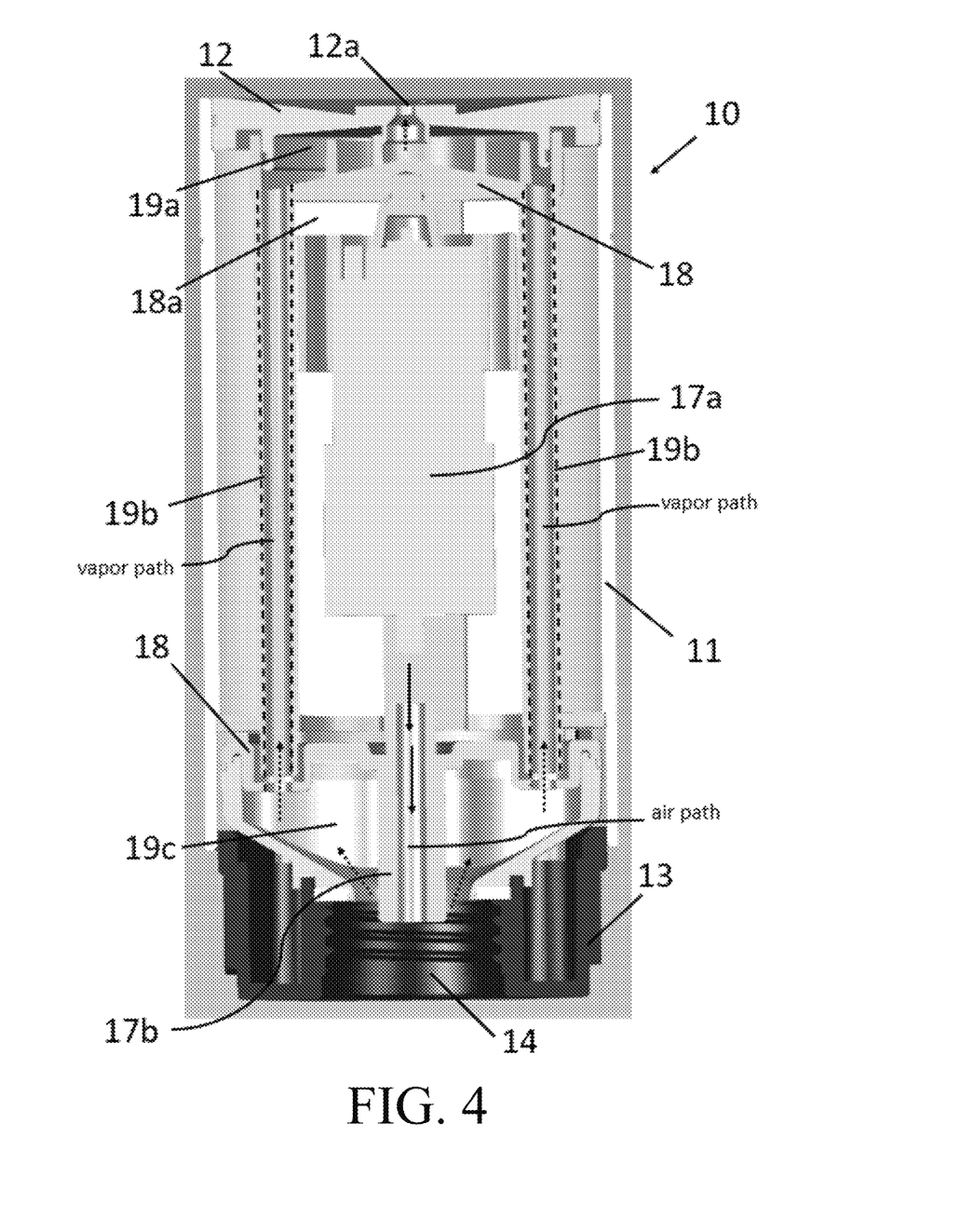
FIG. 4 is a cross-sectional view of the upper portion of FIG. 3.

Referring now to FIGS. 3-4, upper portion 10 may include top cap 12 with top hole 12a, bottom cap 13 having bottom hole 14 and outer connector 16, outer case 11 configured to attach to top cap 12 and bottom cap 13 at opposite ends, and an air tube 17b that extends from air pump 17a. The openings at each end of outer case 11 may define a diameter slightly larger than the diameters of top cap 12 and bottom cap 13 such that outer case 11 may receive and attach to top cap 12 and bottom cap 13 at their respective ends. Bottom hole 14 may be configured to receive and threadably attach to an oil container, e.g., container 70. Bottom cap 13 may further include notches 15 that correspond to similar structures disposed on lower portion 20 (discussed in more detail below) to facilitate the connection between upper portion 10 and lower portion 20 of diffuser 1. Outer case 11 may be a cylinder-like structure with two open ends and configured to house, among other things, air pump 17a and air tube 17b such that air may pass from the air pump to container 70 through the air tube (see solid arrows in FIG. 4) and plug 40. Additionally, outer case 11 may be configured to house vapor tubes 19b and internal components 18 that are arranged to form upper chamber 19a and lower chamber 19c such that vapor passageways (see dotted arrows in FIG. 4) may extend from bottom hole 14 to top hole 12a to channel vaporized oil particles to the top hole of diffuser 1. Lower chamber 19c may receive vapor particles from lower portion 20 through bottom hole 14 and may be arranged to channel the vapor particles to vapor tubes 19b, which may route the vapor pathway around air pump 17a. Each of the vapor tubes 19b may then connect with upper chamber 19a at a top end such that vapor particles pass through upper chamber 19a before exiting diffuser 1. The shape and internal features of upper chamber 19a and lower chamber 19c may be configured to filter vapor particles by trapping heavy vapor particles and letting the lighter vapor particles rise and exit top hole 12a. In this manner, a mist of light vaporized particles may be dispersed from diffuser 1 in a concentrated and controlled way. Furthermore, upper chamber 19a may be arranged with other internal components, e.g., as shown in FIG. 4, such that this hallow chamber may help reduce sound frequency generated by air pump 17a. In this way, diffuser 1 may disperse vaporized particles in a quiet manner.

Figure 5A:
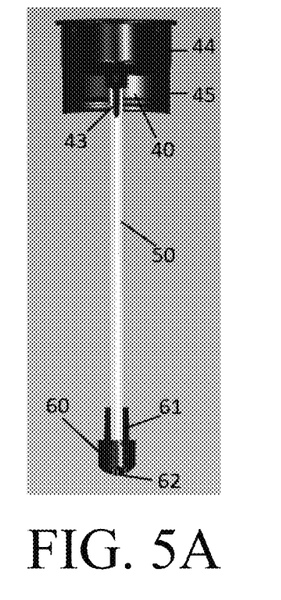
FIG. 5A is a side view of a plug, in accordance with an aspect.
Figure 5B:
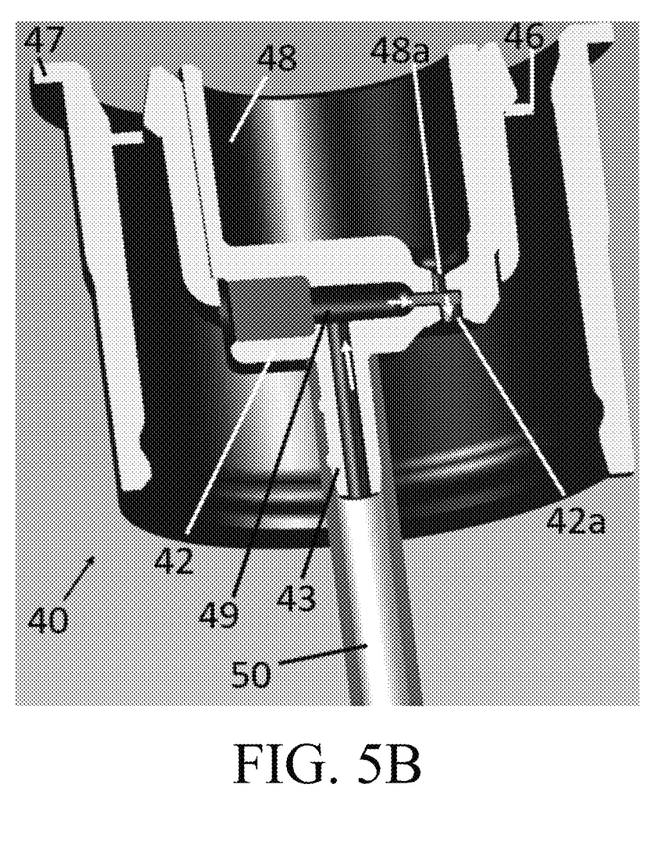
FIG. 5B is a cross sectional view of the plug of FIG. 5A.
Figure 6:
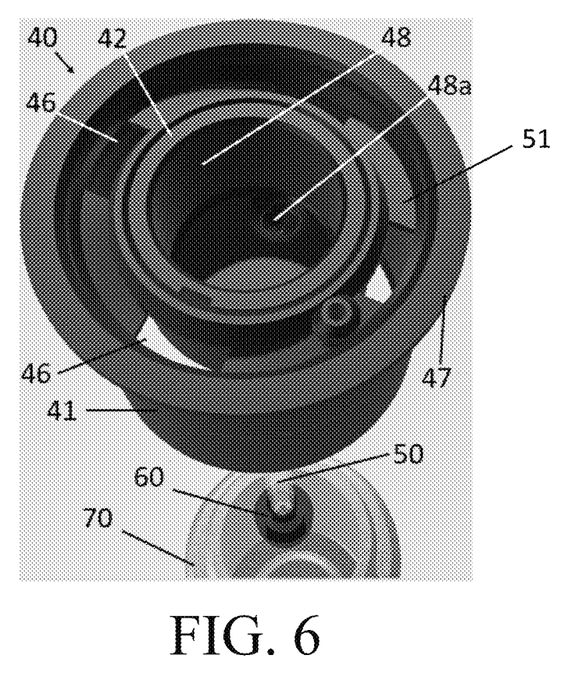
FIG. 6 is a topside view of the plug of FIG. 5A.
Figure 7:
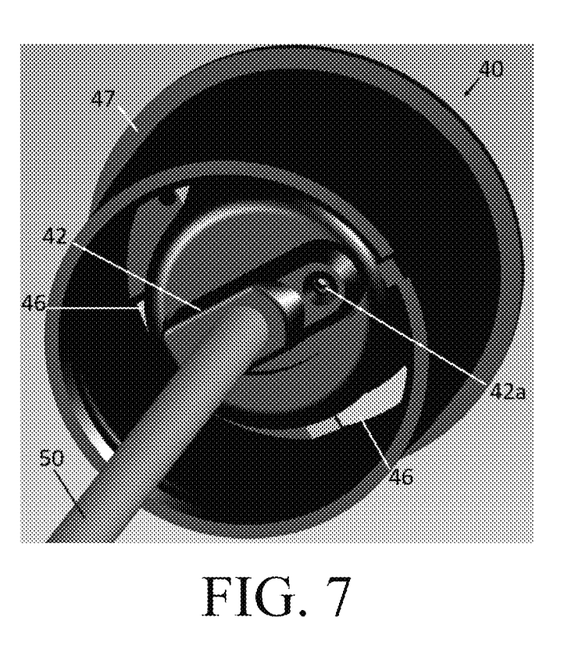
FIG. 7 is an underside view of the plug of FIG. 5A.

Referring now to FIGS. 5A-5B, pipette 50 may be disposed between plug 40 and regulator 60 such that the pipette provides a conduit for oil to move from regulator 60 to plug 40. For example, one open end of pipette 50 may be positioned within neck 61 of regulator 60, and then the other open end of pipette 50 may be attached to plug 40, as shown in FIG. 5A. Alternatively, regulator 60, pipette 50, and plug 40 may be one monolithic component. Regulator 60 may include inlet holes 62 that receive and facilitate the passage of liquid oil from container 70 to a diffuser mechanism, the regulator configured to filter out impurities and separate the oil into smaller droplets drawn into pipette 50. Oil may be pushed into inlet holes 62 in regulator 60 by compressed air in container 70, which may be generated by air pump 17a pumping air into container 70. This compressed air continues to push the oil into regulator 60 and up through pipette 50 until the oil enters atomizer 49 through spout 43 where the oil may be dispersed in a nano particle spray after the oil passes through the atomizer (see white arrows in FIG. 5B). Once dispersed from atomizer 49, the oil particles are forced to flow through exit port 42a by air being pumped into container 70 by air pump 17a through entry port 48a. In this manner, oil may pass thorough regulator 60 and pipette 50 to a diffuser mechanism, e.g., an atomizer, to be vaporized.

Figure 8:
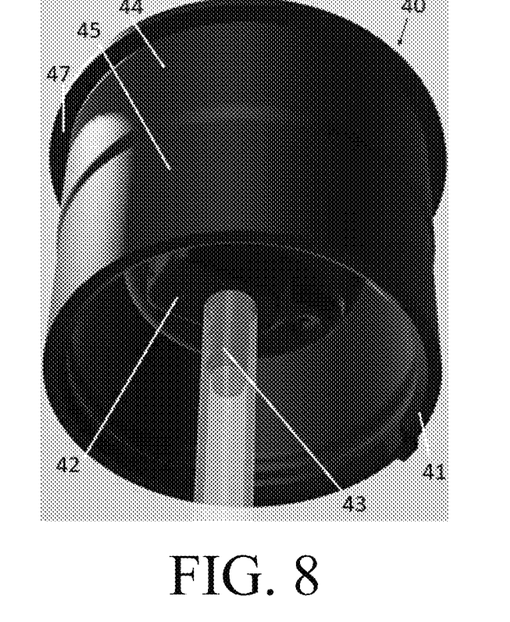
FIG. 8 is another underside view of the plug of FIG. 5A.
Figure 9:
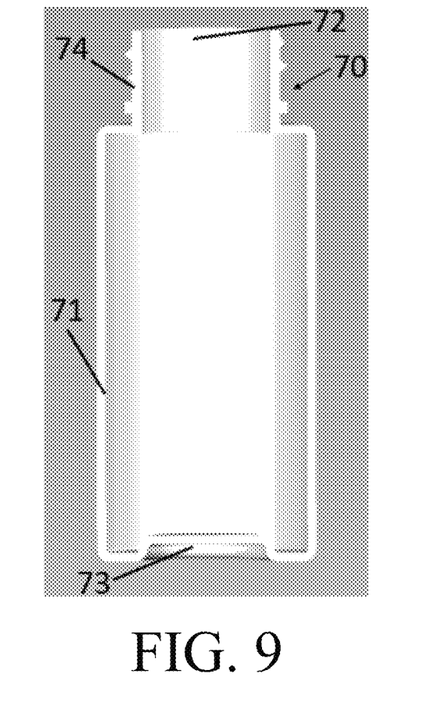
FIG. 9 is a cross-sectional view of a container, in accordance with an aspect.
Figure 10:
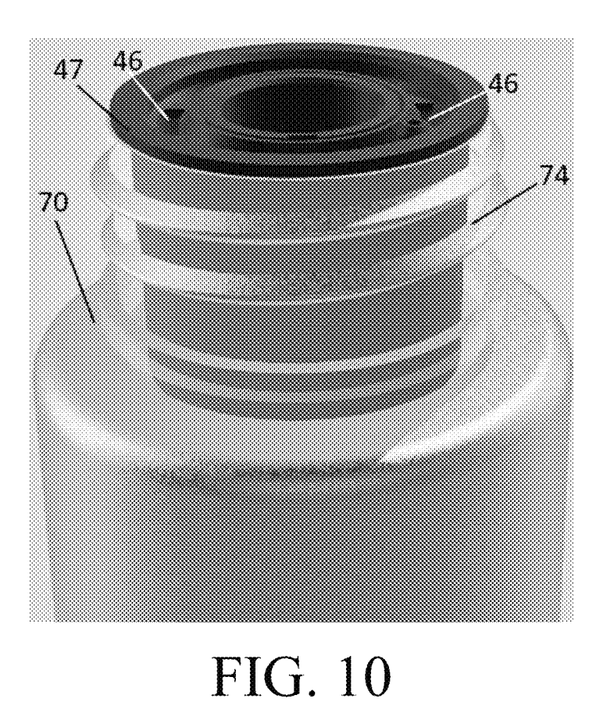
FIG. 10 is a perspective view of the plug of FIG. 5A and the container of FIG. 9 assembled, in accordance with an aspect.

Referring now to FIGS. 5A-8, plug 40 may include an inner portion 42 and outer portion 41 that surrounds the inner portion. Outer portion 41 of plug 40 may be a sleeve-like structure configured with an open end and an internal cavity larger enough to enclose inner portion 42. Vapor vents 46 may be positioned around inner portion 42 and between the inner portion and outer portion 41 such that the structure surrounding vapor vents 46 securely hold the inner portion within the outer portion while vapor vents 46 allow vaporized oil particles to exit container 70 and enter bottom hole 14 of upper portion 10 through vapor vents 46. The exterior of outer portion 41 may include upper section 44 and lower section 45, as shown in FIGS. 5 and 8. Upper section 44 may define an outer diameter larger than an outer diameter of lower section 45 and larger than an inner diameter of container hole 72 (as shown in FIG. 9) such that the outer diameter of the lower section is smaller than the inner diameter of the container hole. The difference between the outer diameter of upper section 44 and the inner diameter of container hole 72 is sufficient enough to establish an interference fit or press fit (i.e., a joint held together by friction) between the upper portion and the container hole while still allowing the upper portion to be fully positioned within container 70. In this manner, container 70 may receive plug 40 such that the plug is irremovably attached to the container, as shown in FIG. 10. It is contemplated that an adhesive may be used in conjunction with the press fit or as an alternative means to secure plug 40 to container 70. It is also contemplated that outer portion 41 could have a tapered shape such that the outer portion starts broad near lip 47 and narrows as the outer portion extends away from the lip in a manner that a press fit between plug 40 and container 70 may be established.

Continuing with references to FIGS. 5A-8, inner portion 42 of plug 40 may house a diffuser mechanism completely enclosed within the inner portion. The diffuser mechanism may vaporize oil or another liquid by cold-air diffusion. For example, atomizer 49 may receive oil in a liquid state at a first end that passes through the atomizer and is released as a nano particle spray at a second end. As mentioned above, compressed air creates a pressure that pushes the oil to and through atomizer 49, which may be generated by air pump 17a. Once released from atomizer 49, the nano particle spray disperses throughout an open-air space within container 70. In this manner, the heavy particles can separate from the lighter particles which rise through vapor vents 46.

Continuing with reference to FIG. 5A-8, spout 43 may extend from inner portion 42 from a bottom side with a tapered exterior and a hollow interior defining an open tunnel that creates a conduit to the diffuser mechanism disposed inside the inner portion. The tapered exterior of spout 43 may be configured such that the spout can be positioned within and attached to pipette 50. In this manner, spout 43 and pipette 50 create a conduit between an oil reservoir and the diffuser mechanism. On the top side of inner portion 42 of plug 40, slot 48 may be disposed and configured to receive air tube 17b of upper portion 10. Slot 48 further includes entry port 48a that allows air pumped through air tube 17b by air pump 17a to enter into container 70 after passing through exit port 42a. The passageway defined by entry port 48a and exit port 42a may be in communication with a diffuser mechanism (e.g., atomizer 49) housed within inner portion 42 such that the air pumped through entry port 48a and 42a causes the vapor particles to flow into container 70 and subsequently rise through vapor vents 46 into upper portion 10 until the vapor disperses from top hole 12a of upper portion 10. In this manner, vapor can be produced within plug 40 and then channeled to top hole 12a of upper portion 10 to be dispersed.

Referring now to FIGS. 9-10, container 70 may be a hollow structure with neck portion 74 and body portion 71 having indentation 73 on the bottom of the container. Neck portion 74 may include container hole 72 that provides access to the hollow interior of container 70. The hollow interior may have a volume of 40 mL or more but preferably at least 60 mL. The exterior of neck portion 74 may be configured to threadably engage bottom hole 14 of upper portion 10 to provide for easy attachment and detachment of container 70 to bottom cap 13 of upper portion 10. As mentioned above, container hole 72 may be configured to receive plug 40 such that an interference fit or press fit is established once the plug is received and lip 47 of plug 40 seats tightly against the outer surface of neck portion 74 to prevent the plug from being positioned too deep within container hole 72, the lip configured to not interfere with the engagement between neck portion 74 and bottom hole 14 of upper portion 10. In this manner, plug 40, pipette 50, and regulator 60 are all irremovably placed within container 70 while the container can be removably attached to upper portion 10 of diffuser 1. An attempt to refill container 70 by removing plug 40 containing atomizer 49 from the container (e.g., a one-time-use fragrance container) may render the container inoperable with the other components of diffuser 1 because frangible members 51 would irreparably break and cause the inner portion of plug 40 to separate apart from the exterior portion of the plug that is fixed within the container. Without an atomizer, container 70 cannot operate with the other components of the diffuser system (i.e., upper portion 10, lower portion 20, etc.) to produce vaporized oil particles. Additionally, plug 40, once positioned within neck portion 74 of container 70, is configured to hinder a user from refilling the container with replacement oil once the initial oil is depleted. For example, the openings of vapor vents 46 may be of a particular dimension that allows vapor particles to exit container 70 but hinders liquid from entering the container. Additionally, the vapor vents may include a grid over the openings of vapor vents 46. Because vapor vents 46 make it impractical to refill container 70 once plug 40 is irremovably installed, a user must obtain a replacement container with oil to continue to use diffuser 1.

Figure 12:
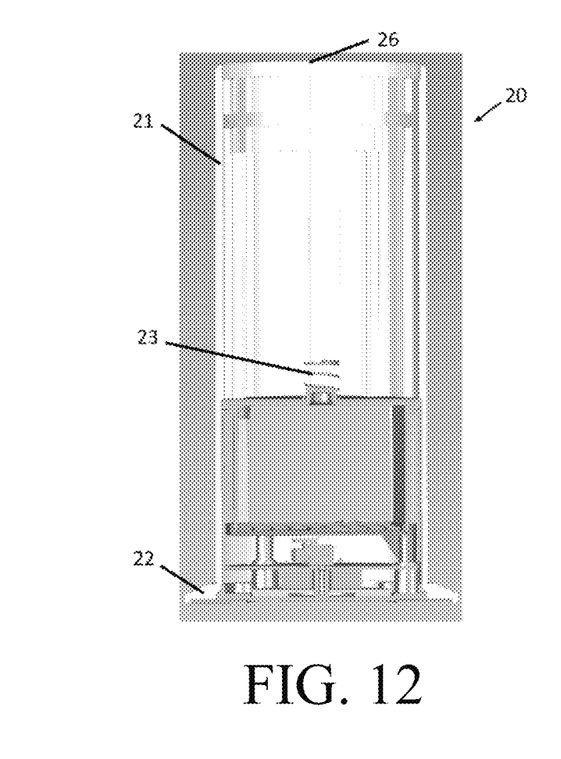
FIG. 12 is a cross-sectional view of the lower portion of FIG. 11.

Referring now to FIGS. 11-12, lower portion 20 may be a hollow cylinder with upper opening 24 defined by outer shell 21 and outer rim 22 disposed at the bottom the lower portion. Outer shell 21 of lower portion 20 may have a smooth and/or textured exterior surface and an interior surface that defines various projections 25 that corresponds to notches 15 disposed on the exterior of bottom cap 13 of upper portion 10 such that the projections of the lower portion and the notches of the upper portion interlock with each other to securely link the upper and lower portions together. The diameter defined by outer shell 21 of lower portion 20 may be substantially equal to the diameter of outer casing 11 of upper portion 10 such that the outer shell is configured to receive bottom cap 13 when the upper and lower portions of diffuser 1 are attached. When bottom cap 13 and container 70 are positioned within lower portion 20, spring 23 may be positioned on an internal structure to engage indention 73 of container 70 to ensure a tight fit between slot 48 of plug 40 and bridge component 17 of upper portion 10. In the event container 70 is not threaded all the way into bottom hole 14, then the internals structure and spring 23 will prevent upper and lower portions from connecting. In this manner, the internal structure and spring 23 ensures that various components of diffuser 1 are properly fit together before operation of the diffuser.

Figure 13:
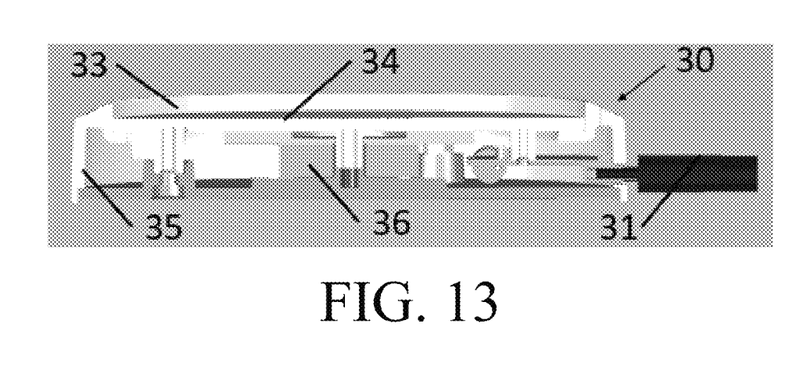
FIG. 13 is a cross-sectional view of a charge associated with the diffuser of FIG. 1.

Continuing with reference to FIGS. 11-12 along with FIG. 13, outer rim 22 may be disposed on the bottom of lower portion 20 to stabilize diffuser 1 when the standing vertically on a surface. Lower portion may further include battery compartment 27 to house a battery or multiple batteries. It is contemplated that such battery or batteries could be either non-rechargeable or rechargeable (e.g., rechargeable Li-Ion battery). In the event a rechargeable battery is incorporated into lower portion 20, the lower portion may be configured such that a battery may be wirelessly charged through induction charging. For example, FIG. 13 shows wireless charger 30 that could be used to wirelessly charge a rechargeable battery incorporated into lower portion 20 of diffuser 1. Outer wall 35 of wireless charger 30 encloses all electrical components 36 need for induction charging. Charger 30 may also include a recessed portion on the top of the charger with proper dimension to fit base 22 within the recess portion.

In some embodiments, a diffuser system may include a one-time-use container with scented oil placed therein, an upper portion of a diffuser, a lower portion of the same diffuser, and a charger. Additionally, because the one-time-use container is none refillable and nonreusable, a diffuser system may include a one-time-use replacement container filled with oil.

In yet another aspect, the present disclosure relates to a method of assembling a one-time-use container. For example, one-time-use container may be assembled by inserting a pipette (e.g., pipette 50) into an oil regulator (e.g., regulator) on one end of the pipette, and then inserting the other end of the pipette onto a spout (e.g., spout 43) extending from an inner portion of a plug (e.g., plug 40). Once the pipette is securely attached to the plug and the regulator, they are inserted into a hollow portion of a container (e.g., container 70) through a hole (e.g., container hole 70) until a lip (e.g., lip 47) extending from the plug abuts a top edge of the container after an interference fit or press fit is formed between an upper section (e.g., upper section 44) of the plug and the hole, as shown in FIG. 10. Additionally, assembling a one-time-use container may include filling the container with scented oil before inserting the plug into the container.

In another aspect, the present invention relates to a method of assembling a diffuser. For example, diffuser may be assembled by threading a one-time-use container that has already been assembled into a bottom hole (e.g., bottom hole 14) of an upper portion (e.g., upper portion 10) until the container is securely affixed to the upper portion and a bridge component (e.g., bridge component 17) is properly slotted into a plug (e.g., plug 40) of the one-time-use container. With the container now affixed to and extending from the bottom of the upper portion, inserting the container into a lower portion (e.g., lower portion 20) of the diffuser and interlocking projections (e.g., projections 25) on the lower portion with corresponding notches (e.g., notches 15) disposed around the bottom end of the upper portion to securely connect the lower and upper portions together such that a spring (e.g., spring 23) disposed within the lower portion is compressed by the container.

It is to be understood that the disclosure set forth herein includes any possible combinations of the particular features set forth above, whether specifically disclosed herein or not. For example, where a particular feature is disclosed in the context of a particular aspect, arrangement, configuration, or arrangement, that feature can also be used, to the extent possible, in combination with and/or in the context of other particular aspects, arrangements, configurations, and arrangements of the technology, and in the technology generally.

Furthermore, although the technology herein has been described with reference to particular features, it is to be understood that these features are merely illustrative of the principles and applications of the present technology. It is therefore to be understood that numerous modifications, including changes in the sizes of the various features described herein, may be made to the illustrative arrangements and that other arrangements may be devised without departing from the spirit and scope of the present technology. In this regard, the present technology encompasses numerous additional features in addition to those specific features set forth in the claims below. Moreover, the foregoing disclosure should be taken by way of illustration rather than by way of limitation as the present technology is defined by the claims set forth below.

The invention claimed is:

1. A diffuser comprising:
an upper portion having an inner connector and an outer connector;
a lower portion having an upper connector at a top end configured to connect to the outer connector of the upper portion, and the lower portion defining an inner cavity;
a fragrance container defining an opening, the fragrance container removably attached to the inner connector of the upper portion and configured to be fit into the inner cavity of the lower portion;
a plug disposed within the opening of the fragrance container to hinder a user from refilling the fragrance container, the plug including an outer portion interconnected to an inner portion by a frangible member; and an atomizer at least partially housed within the inner portion of the plug, wherein the frangible member of the plug is arranged to break when the plug is removed from the fragrance container rendering the fragrance container inoperable.

2. The diffuser of claim 1, wherein the outer portion of the plug is affixed to an inner sidewall of the fragrance container.

3. The diffuser of claim 2, further comprising a pipette having a first end secured to the inner portion of the plug and a second end disposed adjacent a bottom of the fragrance container.

4. The diffuser of claim 3, further comprising a regulator secured to the second end of the pipette.

5. The diffuser of claim 2, wherein the outer portion the plug includes an upper section and a lower section, the upper section having a diameter that is larger than a diameter of the lower section, and wherein the plug is press-fit within the opening of the fragrance container.

6. The diffuser of claim 1, further comprising a base portion disposed at a bottom end of the lower portion that enables the lower portion to stand on a surface such that a longitudinal axis of the lower portion is perpendicular to the surface.

7. The diffuser of claim 6, further comprising a battery disposed within the lower portion, the battery being configured to power the diffuser.

8. The diffuser of claim 7, wherein the battery is a rechargeable battery configured to be recharged by an induction charger having an outer frame configured to receive the base portion.

9. The diffuser apparatus of claim 1, wherein the atomizer defines an inlet port and an outlet disposed entirely within the fragrance container.

10. The diffuser of claim 2, wherein the plug further includes at least one vapor vents disposed between adjacent frangible members.

11. The diffuser of claim 1, wherein the fragrance container further comprises threads for threadably attaching the fragrance container to the inner connector of the upper portion.

12. The diffuser of claim 1, wherein the fragrance container defines a chamber volume of at least 60 mL.

13. The diffuser of claim 1, further comprising a pipette and the atomizer, hollow pipette, and regulator are in communication such that a liquid can enter the regulator and flow to the atomizer through the pipette.

14. The diffuser of claim 5, wherein the diameter of the upper section is at least 1 mm greater than the diameter of the lower section of the plug.

15. A diffuser system, comprising,
a diffuser, comprising:
an upper portion having an inner connector and an outer connector;
a lower portion having an upper connector at a top end configured to connect to the outer connector of the upper portion, the lower portion defining an inner cavity;
a fragrance container defining an opening, the fragrance container removably attached to the inner connector of the upper portion and configured to be fit within the inner cavity of the lower portion, the fragrance container housing a volume of scented liquid;
a plug disposed within the opening of the fragrance container to hinder a user from refilling the fragrance container, the plug including an outer portion interconnected to an inner portion by a frangible member; and
an atomizer at least partially housed within the inner portion of the plug,
wherein the frangible member of the plug is arranged to break when the plug is removed from the fragrance container rendering the fragrance container inoperable.

16. The diffuser system of claim 15, further comprising a one-time-use replacement fragrance container housing a replacement atomizer, the one-time-use replacement fragrance container is configured to attach to the inner connector of the upper portion after the fragrance container is detached from the upper portion of the diffuser.

17. The diffuser system of claim 15, wherein the diffuser further comprises a rechargeable battery.

18. The diffuser system of claim 17, further comprising an induction charger configured to wirelessly charge the rechargeable battery.

* * * * *